United States Patent [19]
Rademaker et al.

[11] Patent Number: 5,397,312
[45] Date of Patent: Mar. 14, 1995

[54] APPLICATOR FOR INTRODUCING A CREAM-TYPE SUBSTANCE INTO A WOMAN'S VAGINA

[75] Inventors: Jacobus J. Rademaker, Nijmegen; Frederique Asberg, Amsterdam, both of Netherlands

[73] Assignee: Akzo N.V., Arnhem

[21] Appl. No.: 61,188

[22] Filed: May 13, 1993

[30] Foreign Application Priority Data

May 15, 1992 [NL] Netherlands ............ 9200861

[51] Int. Cl.$^6$ .................................. A61M 5/315
[52] U.S. Cl. ................... 604/218; 604/187; 604/275; 604/279
[58] Field of Search ............. 604/11, 15, 18, 48, 604/54, 55, 57–60, 187, 218, 310, 311, 264, 275, 279, 207, 225; 222/319, 323, 386

[56] References Cited

U.S. PATENT DOCUMENTS

| | | | |
|---|---|---|---|
| 2,120,367 | 6/1938 | Lewis | 604/311 X |
| 3,297,031 | 1/1967 | Bray | |
| 3,385,300 | 5/1968 | Holter | |
| 3,572,335 | 3/1971 | Robinson | 604/59 X |
| 4,341,211 | 7/1982 | Kline | 128/261 |
| 4,421,504 | 12/1983 | Kline | 604/12 |
| 4,620,534 | 11/1986 | Zartman | 128/127 |
| 4,769,011 | 9/1988 | Swaniger | 604/218 |
| 4,877,037 | 10/1989 | Ko et al. | 128/756 |
| 5,045,058 | 9/1991 | Demetrakopoulos | |
| 5,158,535 | 10/1992 | Paul et al. | 604/15 |

FOREIGN PATENT DOCUMENTS

| | | |
|---|---|---|
| 375265 | 2/1931 | Belgium . |
| 0243250 | 10/1987 | European Pat. Off. . |
| 8404667 | 12/1984 | WIPO . |

*Primary Examiner*—Corrine Maglione
*Attorney, Agent, or Firm*—William M. Blackstone; Mary E. Gormley

[57] ABSTRACT

An applicator for introducing a cream-type substance into a woman's vagina is provided with an elongated holder having at its front end a space for accommodating the substance and a passage opening. A rod-shaped piston shuts off the space at the side facing away from the passage opening and can be operated for pressing the substance through the passage opening out of the space. The holder is transparent and is externally slightly curved in order to facilitate its use. The holder is provided on the outside with a projecting stop plate which limits the part of the holder to be inserted into the vagina. At the side of the stop plate facing away from the passage opening the holder is further provided with a handle which is long enough to be gripped with the whole hand. The holder is also provided on the outside, viewed relative to the radius of curvature, with supporting means for supporting the applicator with the passage opening facing upwards.

18 Claims, 1 Drawing Sheet

APPLICATOR FOR INTRODUCING A CREAM-TYPE SUBSTANCE INTO A WOMAN'S VAGINA

The present invention relates to an applicator for introducing a cream-type substance into a woman's vagina, provided with an elongated holder having at the front end a space for accommodating the substance, and with a passage opening and a rod-shaped piston which shuts off the space at the side facing away from the passage opening and which can be operated to press the substance through the passage opening out of the space.

Such an applicator is known from practice and is used primarily for introducing into the vagina a medication for local urogenital conditions in menopausal women. The applicator comprises a thin, straight cylindrical holder and is intended for repeated use. For the introduction of the cream-type substance into the space designed for it, the tip of a special tube is screwed into the passage opening and then pinched, with the result that the cream-type substance flows into the space and presses back the rod-shaped cylinder until it goes against a stop. The correct dosage must then be reached. The introduction of the applicator into the vagina by the woman herself is best achieved if she lies on her back. The holder is then held between the thumb, middle and ring fingers, while the piston rod is operated by the index finger.

The object of the invention is now to improve the known applicator further, in particular as regards ease of use.

According to a first aspect of the invention, the applicator is for this purpose characterised in that at least the part of the holder to be inserted into the vagina is slightly curved, externally at any rate.

This curvature of the holder means, on the one hand, that it follows the natural contours of the vagina, and the shape inspires confidence in the woman. On the other hand, the upward curvature during use will ensure that the operating end of the holder projects upwards more and is thus closer up, as a result of which it is easier to reach, and is thus easier to operate. The curvature will preferably be approximately 200–300 mm.

The cross-section of the part of the holder to be inserted into the vagina according to the invention will lie between 14 and 25 mm, and will preferably be oval-shaped, the main axis lying in the plane of the curvature. The inside of the holder, on the other hand, is preferably circular in cross-section because the piston then fits into the holder in all turned positions, and consequently no fitting mistakes can be made.

It is an advantage if according to a further aspect of the invention the holder is provided on the outside with a projecting stop plate limiting the part of the holder to be introduced into the vagina.

This measure means that the woman does not need to determine the insertion depth herself, and the holder can be inserted up to the point where the stop plate comes to rest against, for example, the perineum. This is the correct depth.

The invention further proposes that at the outside, viewed relative to the radius of curvature, the holder should be provided with supporting means for supporting the applicator with the passage opening facing upwards. These supporting means make it possible to set down the applicator for a moment, for example after filling with the cream-type substance, without the applicator rolling away or the cream-type substance dripping out of the passage opening again. It is pointed out that the supporting means can, of course, also be used on a straight holder, in which case the supports must then be dimensioned in such a way that the holder stands up slanting in the direction of the passage opening.

It is also preferable for the holder to be at least partially transparent, while it is possible to provide both the holder and the piston with interacting markings.

In this way a visual check can be made during filling of the space in the holder with cream-type substance, which will lead to a reduction in mistakes in the dosage.

These mistakes are further reduced if the piston and the holder are provided with interacting snap elements for holding the piston in at least one position relative to the holder.

With the aid of these snap elements the piston, for example, can be already set before filling in a position in which the volume of the space is equal to the dosage of the substance. This space need then only be filled with the substance, for example by injecting the substance from a tube.

The invention will be explained in greater detail below with reference to the drawing, which shows an example of an embodiment of the applicator according to the invention.

Figure 1:
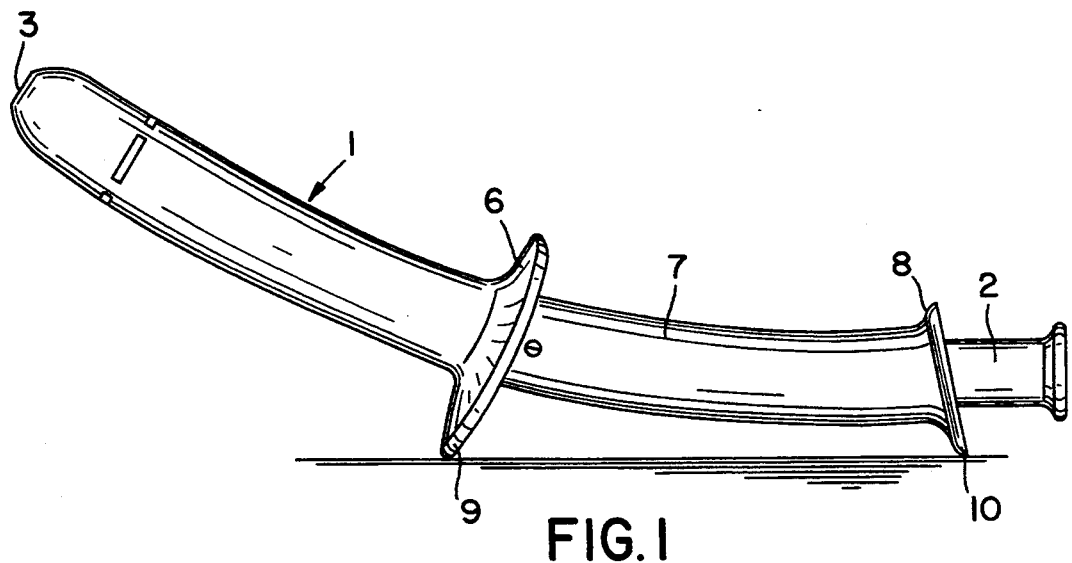
FIG. 1 is a side view of the example of an embodiment of the applicator for introducing a medicinal cream into a woman's vagina.

The drawing shows an example of an embodiment of an applicator which is intended in the first instance for the introduction of a medicinal cream into the vagina to control urogenital conditions in menopausal women, but other applications where some cream-type substance or other must be administered at a certain place in the vagina are, of course, also conceivable. The woman has to be able to operate the applicator herself.

The applicator is in principle made up of two parts, a holder 1 and a rod-shaped piston 2 which is movable therein. The holder 1 is injection moulded from a rigid plastic such as polycarbonate and, although this is not shown in the drawing, is preferably transparent, so that the user can see into the inside of the holder 1.

Figure 2:
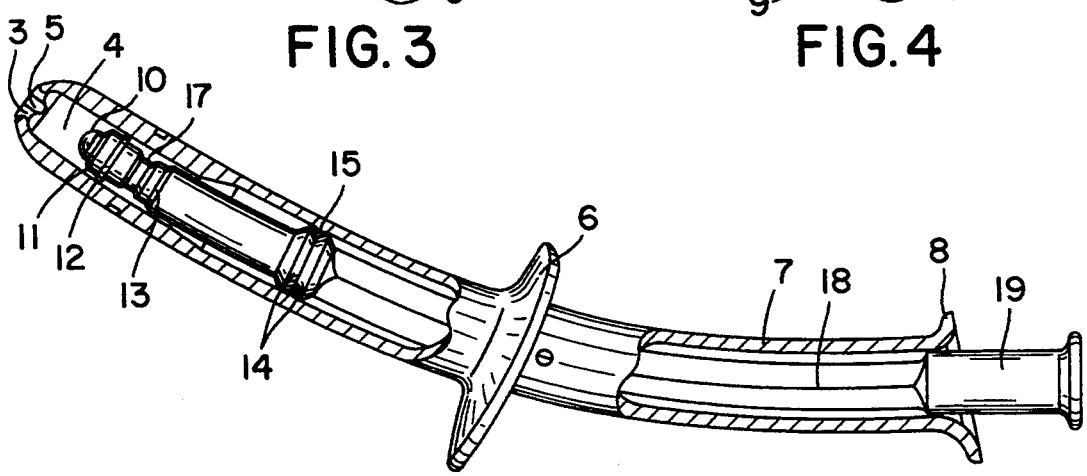
FIG. 2 is a side view corresponding to FIG. 1, in which the holder of the applicator is largely cut away.

As can be seen clearly in FIGS. 1 and 2, the holder 1 is curved in shape over its entire length. The radius of curvature corresponds approximately to the average upward curve of a penis, with the result that the holder fits in well with the shape of the vagina and the shape inspires confidence in the user. In the example of an embodiment shown the radius of curvature is about 250 mm. Of course, it could also be possible to make the holder 1 curved along only a part, for example only the part which is introduced into the vagina.

At the front end of the holder 1 (left side in FIGS. 1 and 2) there is a passage opening 3, behind which there is a space 4 (FIG. 2) for accommodation of the cream. The passage opening 3 is used both for introduction of the cream for filling the space 4 and for allowing through the cream from the space 4 when it is being administered to the vagina. The passage opening 3 has a round cross-section, but is provided with two opposite, lateral cavities 5 designed to allow air to escape from the space 4 when the cream is being introduced from a tube into the space 4 and the tube is projecting with the tip fitting in the passage opening 3.

The holder 1 is rounded in shape all round the passage opening 3, and at the front end tapers slightly in order to facilitate introduction into the vagina. The rounded shapes also help to ensure that the woman is less afraid of hurting herself, which reduces the fear of using the applicator for the first time.

At a distance from the front end of the holder 1 is a collar-shaped stop plate 6 on the outside of the holder 1, which is used to limit the insertion depth of the holder. The insertion depth in the present example is approximately 80 mm. The position of the stop plate 6 is selected in such a way that the correct insertion depth of the holder 1 is reached when the stop plate 6 falls against the horseshoe-shaped sphincter at the bottom side of the vaginal opening (in the direction of the anus). This area, the perineum, can provide the stop plate 6 with most support. When the stop plate 6 goes against it, the woman feels that the correct insertion depth has been reached. The stop plate is at a slight angle to the radius of curvature of the holder 1, which angle is approximately 5° in the example of an embodiment shown. This angle increases the stability of the applicator and the front face of the stop plate 6 fits better against the labia of the vagina after the holder 1 is inserted. This stop plate 6 again is rounded in shape.

The part of the holder 1 at the side of the stop plate 6 facing away from the passage opening 3 is intended as a handle 7 and is dimensioned in such a way that the handle can be gripped either with the thumb and middle finger alone or with the whole hand. In the latter case the little finger side of the hand can rest against the stop plate 6 and on insertion of the holder 1 in the vagina can come into contact with the labia, which means that an additional tactile check on the correct insertion depth is present. The rear end of the holder 1 limiting the handle 7 is designed with a collar 8 which, like the stop plate 6, lies at a slight angle to the radius of curvature of the holder 1, which slightly increases its accessibility. At right angles to the radius of curvature of the holder 1 the collar 8 is slightly curved, making the collar 8 lie better in the hand.

Figure 3:
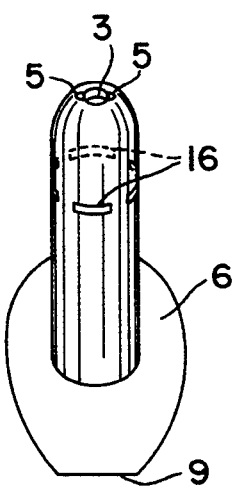
FIG. 3 is a front view of the applicator according to FIG. 1.
Figure 4:
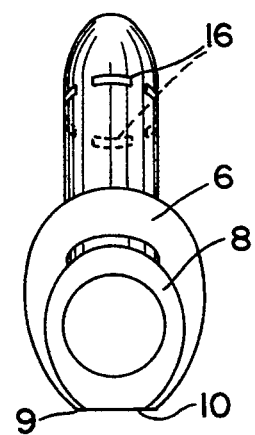
FIG. 4 is a rear view of the applicator according to FIG. 1.

As can be seen in FIGS. 3 and 4, both the stop plate 6 and the collar 8 at the side facing away from the centre of curvature of the holder 1 are provided with a flattened part 9, 10, which together form a supporting face for the applicator, by means of which the applicator can be set down, in such a way that the passage opening 3 is lying slanted upwards. This prevents the applicator from rolling away, and in the standing position shown in FIG. 1 no cream can run out of the space 4 when the user sets down the applicator, for example in order to screw the cap on the cream tube. It can also be seen from a comparison of, for example, FIG. 3 and FIG. 1 that the external cross-section of the holder 1 is slightly oval, the main axis lying in the plane of the radius of curvature of the holder 1. The smallest cross-section of the holder 1 in this example of an embodiment is 14 mm, while the cross-section along the main axis is 15 mm. The external cross-section of the holder 1 is preferably constant over the entire length, in particular at its insertion part.

The design of the rod-shaped piston 2 can be seen in FIG. 2. The piston 2 is made from a flexible material, so that the piston 2 can be made straight and through bending can adapt to the curvature of the holder during its insertion into said holder. The working front part of the piston 2 has a circular cross-section, which also applies to the inside of the holder 1. At the front end of the piston 2 lies a convex projection 10, whose diameter and shape correspond approximately to those of the passage opening 3, so that the projection 10 fits into the passage opening 3 and all cream can thus be pressed out of the space 4 and out of the passage opening 3. Two sealing edges 11, 12 which seal off the piston 2 against the inside of the holder 1 are provided directly behind the projection 10. In this case the first sealing edge 11 limits the space 4 in the holder 1, and the second sealing edge is provided as a reserve. Since the piston 2 is made of fairly soft material, the sealing edges 11, 12 can be slightly oversized relative to the internal diameter of the holder 1 at the position of the space 4, so that a good sealing effect is achieved. An edge 13 placed at some distance behind the second sealing edge 12 in interaction therewith serves as a guide of the piston 2 in the holder 1.

Snap or locking elements 14 are provided on the outer periphery of the piston 2 at a distance behind the third edge 13 of the piston 2, which elements interact with a counter element 15 on the inner periphery of a part of the inside of the holder 1 which has a greater diameter than the space 4. The snap elements 14 comprise two spring-loaded rings with slanting run-on edges, between which the counter element 15 of the holder, in the form of an internal annular projection, can be clamped, so that in that position the user can feel that the piston 2 is held in position relative to the holder 1. In this snapped-in position the piston 2 is in such a position that the space 4 limited by the piston 2 has a volume which corresponds to the correct dosage of the cream to be introduced. Before the introduction of the cream into the space, the piston 2 is therefore first snapped into place, following which the cream can be pressed through the passage opening 3 into the space 4. The piston 2 in this case need not be moved to a stop, and can simply remain in the snapped-in position. This guarantees the correct dosage of the cream. Due to the fact that in most cases the holder 1 is transparent, a visual check can be made on whether the counter element 15 of the holder 1 is lying between the snap elements 14 of the piston. An additional visual check is also provided through both the holder 1 and the piston. 2 being provided with gauge marks. A broken gauge mark 16 is provided on the outside of the transparent holder 1, while the piston has a narrowed part with continuous gauge mark 17. In the correct filled position of the piston 2 the two gauge marks 16 and 17 overlap, which is easy to see because of the fact that the gauge mark 16 on the holder 1 is broken.

The piston 2 also has further backwards a rod part 18, and at the rear end has a control button 19 for operating the piston 2 with the thumb or the index finger. The rod part is cross-shaped in cross-section, in order to save material and to increase the flexibility of the piston.

The manufacture of both the holder and the piston is preferably by injection moulding, as stated above. The requirements set for the material of the holder 1 are: transparency, impact resistance, heat resistance to at least 90°C., suitability for this pharmaceutical application, and the material must be recyclable or destructible. The surface must be such that it can be made smooth and polish-finished, and the material must preferably be such that it can be coloured. Polycarbonate or polystyrene are materials which can meet all these requirements, while these materials are durable, with the result that the applicator will last longer. It can be used for at least 120 applications. The piston 2 must be such that it can be made by injection moulding and can be coloured, and it must be resistant to boiling water. It must also be flexible, so that the piston can be bent easily in the curved holder 1. On account of these requirements, high-density polyethylene, which is also recyclable and cheap, can be selected. Alternatively, when the curved piston 2 is not flexible, the holder 1 must be flexible.

For injection moulding of the holder 1 in one go, a four-part mould is used, one for the insertion part of the holder 1 in front of the stop plate 6, two for the handle 7 of the holder 1, and one for the inside of the holder. The single mould part for the insertion part of the holder means that there is no part seam on its surface. The mould for the piston can simply consist of two parts. The continuous gauge mark on the head of the piston 2 can be printed on by means of flexographic printing, while the broken gauge mark on the holder 1 of the applicator can be applied most simply by the tampon printing technique, which is specially suitable for curved surfaces. The gauge marks are preferably black.

It will be clear from the above that the invention provides an applicator for introducing a cream-type substance into the vagina which is outstanding through its user friendliness and provides a good guarantee for the correct dosage, while the applicator is also easy to clean after each use.

The invention is not limited to the example of an embodiment shown in the drawing and described above, which can be varied in different ways within the scope of the invention.

What is claimed is:

1. Applicator for introducing a cream-type substance into a woman's vagina, comprising an elongated holder having a front end and a back end and an internal space extending through the length thereof and opening at each end forming a passage, and a rod-shaped piston extending into the interior space from the back end, which can be operated to push a substance located within the interior space through the passage, wherein at least the front part of the holder, which is to be inserted into the vagina, is slightly curved, and wherein both the holder and the piston are provided with interacting markings.

2. Applicator according to claim 1, wherein the radius of curvature of the holder is approximately 200–300 mm.

3. Applicator according to claim 1, wherein the cross-section of the part of the holder to be inserted into the vagina has a width of between 14 and 25 mm.

4. Applicator according to claim 1, wherein the interior space of the part of the holder, which is to be inserted into the vagina, has a circular cross-section and the exterior of said part has an oval cross-section with the main axis in the plane of curvature.

5. Applicator according to claim 1, wherein the holder is provided on the outside with a projecting stop plate, which limits the part of the holder that may be introduced into the vagina.

6. Applicator according to claim 1, wherein the side of the stop plate facing the back end of the holder is provided with a handle that is long enough to be gripped by the whole hand of a woman.

7. Applicator according to claim 1, wherein the holder, viewed relative to the radius of curvature, is provided on the exterior of said holder with supporting means for supporting the applicator with the front end facing upwards.

8. Applicator according to claim 1, wherein the holder is at least partially transparent.

9. Applicator according to claim 1, wherein the piston and the holder are provided with interacting snap elements for holding the piston in at least one position relative to the holder.

10. Applicator for introducing a cream-type substance into a woman's vagina, comprising an elongated holder having a front end and a back end and an internal space extending through the length thereof and opening at each end forming a passage, and a rod-shaped piston extending into the interior space from the back end, which can be operated to push a substance located within the interior space through the passage, and having on the outside of said holder a projecting stop plate, which limits the part of the holder that may be introduced into the vagina, wherein at least the front part of the holder, which is to be inserted into the vagina, is curved with a radius of curvature of approximately 200–300 mm, and said stop plate is not in line with said radius of curvature.

11. Applicator according to claim 10, in which the cross-section of the part of the holder to be inserted into the vagina has a width of between 14 and 25 mm.

12. Applicator according to claim 10, in which the interior space of the part of the holder to be inserted into the vagina has a circular cross-section and the exterior of said part has an oval cross-section with the main axis in the plane of the curvature.

13. Applicator according to claim 10, in which a handle is provided extending from the side of the stop plate facing the back end of the holder, wherein said handle is long enough to be gripped by the whole hand of a woman.

14. Applicator according to claim 10, in which the holder, viewed relative to the radius of curvature, is provided on the exterior of the hold with supporting means for supporting the applicator with the front end facing upwards.

15. Applicator according to claim 10, in which the holder is at least partially transparent.

16. Applicator according to claim 15, in which both the holder and the piston are provided with interacting markings.

17. Applicator according to claim 10, in which the piston and the holder are provided with interacting snap elements for holding the piston in at least one position relative to the holder.

18. Applicator according to claim 10, wherein the stop plate is at an angle of approximately 5° to the radius of curvature of the holder.

* * * * *